(12) United States Patent
Tabuteau

(10) Patent No.: US 12,390,428 B2
(45) Date of Patent: *Aug. 19, 2025

(54) BUPROPION AND DEXTROMETHORPHAN FOR REDUCTION OF SUICIDE RISK IN DEPRESSION PATIENTS

(71) Applicant: ANTECIP BIOVENTURES II LLC, New York, NY (US)

(72) Inventor: Herriot Tabuteau, New York, NY (US)

(73) Assignee: ANTECIP BIOVENTURES II LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/397,220

(22) Filed: Dec. 27, 2023

(65) Prior Publication Data
US 2024/0390297 A1    Nov. 28, 2024

Related U.S. Application Data

(63) Continuation of application No. 18/323,714, filed on May 25, 2023, now Pat. No. 11,896,563, which is a continuation of application No. PCT/US2021/061492, filed on Dec. 1, 2021.

(60) Provisional application No. 63/120,160, filed on Dec. 1, 2020, provisional application No. 63/120,672, filed on Dec. 2, 2020, provisional application No. 63/122,902, filed on Dec. 8, 2020.

(51) Int. Cl.
A61K 31/137    (2006.01)
A61K 31/485    (2006.01)
A61P 25/24     (2006.01)

(52) U.S. Cl.
CPC .......... *A61K 31/137* (2013.01); *A61K 31/485* (2013.01); *A61P 25/24* (2018.01)

(58) Field of Classification Search
CPC ...... A61K 31/137; A61K 31/485; A61P 25/24
See application file for complete search history.

(56) References Cited

U.S. PATENT DOCUMENTS

| | | |
|---|---|---|
| 5,358,970 A | 10/1994 | Ruff et al. |
| 5,731,000 A | 3/1998 | Ruff et al. |
| 5,763,493 A | 6/1998 | Ruff et al. |
| 6,306,436 B1 | 10/2001 | Chungi et al. |
| 6,780,871 B2 | 8/2004 | Glick et al. |
| 8,088,786 B2 | 1/2012 | McKinney et al. |
| 8,569,328 B1 | 10/2013 | Tabuteau |
| 9,168,234 B2 | 10/2015 | Tabuteau |
| 9,198,905 B2 | 12/2015 | Tabuteau |
| 9,205,083 B2 | 12/2015 | Tabuteau |
| 9,238,032 B2 | 1/2016 | Tabuteau |
| 9,278,095 B2 | 3/2016 | Tabuteau |
| 9,314,462 B2 | 4/2016 | Tabuteau |
| 9,370,513 B2 | 6/2016 | Tabuteau |
| 9,375,429 B2 | 6/2016 | Tabuteau |
| 9,402,843 B2 | 8/2016 | Tabuteau |
| 9,402,844 B2 | 8/2016 | Tabuteau |
| 9,408,815 B2 | 8/2016 | Tabuteau |
| 9,421,176 B1 | 8/2016 | Tabuteau |
| 9,457,023 B1 | 10/2016 | Tabuteau |
| 9,457,025 B2 | 10/2016 | Tabuteau |
| 9,474,731 B1 | 10/2016 | Tabuteau |
| 9,486,450 B2 | 11/2016 | Tabuteau |
| 9,700,528 B2 | 7/2017 | Tabuteau |
| 9,700,553 B2 | 7/2017 | Tabuteau |
| 9,707,191 B2 | 7/2017 | Tabuteau |
| 9,763,932 B2 | 9/2017 | Tabuteau |
| 9,861,595 B2 | 1/2018 | Tabuteau |
| 9,867,819 B2 | 1/2018 | Tabuteau |
| 9,968,568 B2 | 5/2018 | Tabuteau |
| 10,058,518 B2 | 8/2018 | Tabuteau |
| 10,064,857 B2 | 9/2018 | Tabuteau |
| 10,080,727 B2 | 9/2018 | Tabuteau |
| 10,092,560 B2 | 10/2018 | Tabuteau |
| 10,092,561 B2 | 10/2018 | Tabuteau |
| 10,105,327 B2 | 10/2018 | Tabuteau |

(Continued)

FOREIGN PATENT DOCUMENTS

| | | |
|---|---|---|
| BR | 102016010170 A2 | 11/2017 |
| EP | 4183391 A1 | 5/2023 |

(Continued)

OTHER PUBLICATIONS

Spravato (esketamine), Highlights of Prescribing Information, revised Jul. 2020.
Nuedexta (dextromethorphan hydrobromide and quinidine sulfate), Highlights of Prescribing Information, revised Dec. 2022.
Aplenzin (bupropion hydrobromide), Highlights of Prescribing Information, revised Mar. 2022.
Tod et al., Quantitative Prediction of Cytochrome P450 (CYP) 2D6-Mediated Drug Interactions, Clinical Pharmacokinetics, 50(8), 519-530, Aug. 2011.
Kotlyar et al., Inhibition of CYP2D6 Activity by Bupropion, Journal of Clinical Psychopharmacology, 25(2), 226-229, Jun. 2005.
Pope et al., Pharmacokinetics of Dextromethorphan after Single or Multiple Dosing in Combination with Quinidine in Extensive and Poor Metabolizers, The Journal of Clinical Pharmacology, 44(10), 1132-1142, Oct. 2004.

(Continued)

*Primary Examiner* — Kevin E Weddington
(74) *Attorney, Agent, or Firm* — PROCOPIO, CORY, HARGREAVES & SAVITCH LLP; Brent Johnson; Yuefen Zhou

(57) ABSTRACT

This disclosure relates to a method of treating depression and/or reducing risk of suicide, comprising administering a combination of about 90 mg to about 120 mg of bupropion hydrochloride, or a molar equivalent amount of another form of bupropion, and about 40 mg to about 50 mg of dextromethorphan hydrobromide, or a molar equivalent amount of another form of dextromethorphan. The combination may be administered twice a day to a human being suffering from major depressive disorder and having a score of 3 or greater on the Suicidality Item of the Montgomery-Åsberg Depression Rating Scale (MADRS-SI).

17 Claims, No Drawings

(56) References Cited

U.S. PATENT DOCUMENTS

| | | |
|---|---|---|
| 10,105,361 B2 | 10/2018 | Tabuteau |
| 10,251,879 B2 | 4/2019 | Tabuteau |
| 10,463,634 B2 | 11/2019 | Tabuteau |
| 10,512,643 B2 | 12/2019 | Tabuteau |
| 10,548,857 B2 | 2/2020 | Tabuteau |
| 10,596,167 B2 | 3/2020 | Tabuteau |
| 10,688,066 B2 | 6/2020 | Tabuteau |
| 10,695,304 B2 | 6/2020 | Tabuteau |
| 10,772,850 B2 | 9/2020 | Tabuteau |
| 10,780,064 B2 | 9/2020 | Tabuteau |
| 10,780,066 B2 | 9/2020 | Tabuteau |
| 10,786,469 B2 | 9/2020 | Tabuteau |
| 10,786,496 B2 | 9/2020 | Tabuteau |
| 10,799,497 B2 | 10/2020 | Tabuteau |
| 10,806,710 B2 | 10/2020 | Tabuteau |
| 10,813,924 B2 | 10/2020 | Tabuteau |
| 10,864,209 B2 | 12/2020 | Tabuteau |
| 10,874,663 B2 | 12/2020 | Tabuteau |
| 10,874,664 B2 | 12/2020 | Tabuteau |
| 10,874,665 B2 | 12/2020 | Tabuteau |
| 10,881,624 B2 | 1/2021 | Tabuteau |
| 10,881,657 B2 | 1/2021 | Tabuteau |
| 10,894,046 B2 | 1/2021 | Tabuteau |
| 10,894,047 B2 | 1/2021 | Tabuteau |
| 10,898,453 B2 | 1/2021 | Tabuteau |
| 10,925,842 B2 | 2/2021 | Tabuteau |
| 10,933,034 B2 | 3/2021 | Tabuteau |
| 10,940,124 B2 | 3/2021 | Tabuteau |
| 10,945,973 B2 | 3/2021 | Tabuteau |
| 10,966,941 B2 | 4/2021 | Tabuteau |
| 10,966,942 B2 | 4/2021 | Tabuteau |
| 10,966,974 B2 | 4/2021 | Tabuteau |
| 10,980,800 B2 | 4/2021 | Tabuteau |
| 11,007,189 B2 | 5/2021 | Tabuteau |
| 11,020,389 B2 | 6/2021 | Tabuteau |
| 11,058,648 B2 | 7/2021 | Tabuteau |
| 11,065,248 B2 | 7/2021 | Tabuteau |
| 11,090,300 B2 | 8/2021 | Tabuteau |
| 11,096,937 B2 | 8/2021 | Tabuteau |
| 11,123,343 B2 | 9/2021 | Tabuteau |
| 11,123,344 B2 | 9/2021 | Tabuteau |
| 11,129,826 B2 | 9/2021 | Tabuteau |
| 11,141,388 B2 | 10/2021 | Tabuteau |
| 11,141,416 B2 | 10/2021 | Tabuteau |
| 11,147,808 B2 | 10/2021 | Tabuteau |
| 11,185,515 B2 | 11/2021 | Tabuteau |
| 11,191,739 B2 | 12/2021 | Tabuteau |
| 11,197,839 B2 | 12/2021 | Tabuteau |
| 11,207,281 B2 | 12/2021 | Tabuteau |
| 11,213,521 B2 | 1/2022 | Tabuteau |
| 11,229,640 B2 | 1/2022 | Tabuteau |
| 11,234,946 B2 | 2/2022 | Tabuteau |
| 11,253,491 B2 | 2/2022 | Tabuteau |
| 11,253,492 B2 | 2/2022 | Tabuteau |
| 11,273,133 B2 | 3/2022 | Tabuteau |
| 11,273,134 B2 | 3/2022 | Tabuteau |
| 11,285,118 B2 | 3/2022 | Tabuteau |
| 11,285,146 B2 | 3/2022 | Tabuteau |
| 11,291,638 B2 | 4/2022 | Tabuteau |
| 11,291,665 B2 | 4/2022 | Tabuteau |
| 11,298,351 B2 | 4/2022 | Tabuteau |
| 11,298,352 B2 | 4/2022 | Tabuteau |
| 11,311,534 B2 | 4/2022 | Tabuteau |
| 11,344,544 B2 | 5/2022 | Tabuteau |
| 11,357,744 B2 | 6/2022 | Tabuteau |
| 11,364,233 B2 | 6/2022 | Tabuteau |
| 11,382,874 B2 | 7/2022 | Tabuteau |
| 11,419,867 B2 | 8/2022 | Tabuteau |
| 11,426,370 B2 | 8/2022 | Tabuteau |
| 11,426,401 B2 | 8/2022 | Tabuteau |
| 11,433,067 B2 | 9/2022 | Tabuteau |
| 11,439,636 B1 | 9/2022 | Tabuteau |
| 11,478,468 B2 | 10/2022 | Tabuteau |
| 11,497,721 B2 | 11/2022 | Tabuteau |
| 11,510,918 B2 | 11/2022 | Tabuteau |
| 11,517,542 B2 | 12/2022 | Tabuteau |
| 11,517,543 B2 | 12/2022 | Tabuteau |
| 11,517,544 B2 | 12/2022 | Tabuteau |
| 11,524,007 B2 | 12/2022 | Tabuteau |
| 11,524,008 B2 | 12/2022 | Tabuteau |
| 11,534,414 B2 | 12/2022 | Tabuteau |
| 11,541,021 B2 | 1/2023 | Tabuteau |
| 11,541,048 B2 | 1/2023 | Tabuteau |
| 11,571,399 B2 | 2/2023 | Tabuteau |
| 11,571,417 B2 | 2/2023 | Tabuteau |
| 11,576,877 B2 | 2/2023 | Tabuteau |
| 11,576,909 B2 | 2/2023 | Tabuteau |
| 11,590,124 B2 | 2/2023 | Tabuteau |
| 11,596,627 B2 | 3/2023 | Tabuteau |
| 11,617,728 B2 | 4/2023 | Tabuteau |
| 11,617,747 B2 | 4/2023 | Tabuteau |
| 11,628,149 B2 | 4/2023 | Tabuteau |
| 11,660,273 B2 | 5/2023 | Tabuteau |
| 11,660,274 B2 | 5/2023 | Tabuteau |
| 11,717,518 B1 | 8/2023 | Tabuteau |
| 11,730,706 B1 | 8/2023 | Tabuteau |
| 11,752,144 B1 | 9/2023 | Tabuteau |
| 11,779,579 B2 | 10/2023 | Tabuteau |
| 11,839,612 B1 | 12/2023 | Tabuteau |
| 11,844,797 B1 | 12/2023 | Tabuteau |
| 11,883,373 B1 | 1/2024 | Tabuteau |
| 11,896,563 B2 * | 2/2024 | Tabuteau ................ A61P 25/24 |
| 11,925,636 B2 | 3/2024 | Tabuteau |
| 11,969,421 B2 | 4/2024 | Tabuteau |
| 11,986,444 B2 | 5/2024 | Tabuteau |
| 12,036,191 B1 | 7/2024 | Tabuteau |
| 12,042,473 B2 | 7/2024 | Tabuteau |
| 12,109,178 B2 | 10/2024 | Tabuteau |
| 12,138,260 B2 | 11/2024 | Tabuteau |
| 12,146,889 B1 | 11/2024 | Tabuteau |
| 12,194,005 B2 | 1/2025 | Tabuteau |
| 12,194,006 B2 | 1/2025 | Tabuteau |
| 12,194,036 B2 | 1/2025 | Tabuteau |
| 2002/0035105 A1 | 3/2002 | Caruso |
| 2003/0044462 A1 | 3/2003 | Subramanian et al. |
| 2008/0044462 A1 | 2/2008 | Trumbore et al. |
| 2010/0040679 A1 | 2/2010 | Chang |
| 2010/0291225 A1 | 11/2010 | Fanda et al. |
| 2015/0126541 A1 | 5/2015 | Tabuteau |
| 2015/0126542 A1 | 5/2015 | Tabuteau |
| 2015/0126543 A1 | 5/2015 | Tabuteau |
| 2015/0126544 A1 | 5/2015 | Tabuteau |
| 2015/0133485 A1 | 5/2015 | Tabuteau |
| 2015/0133486 A1 | 5/2015 | Tabuteau |
| 2015/0150830 A1 | 6/2015 | Tabuteau |
| 2015/0157582 A1 | 6/2015 | Tabuteau |
| 2015/0342947 A1 | 12/2015 | Pollard et al. |
| 2016/0008352 A1 | 1/2016 | Tabuteau |
| 2016/0030420 A1 | 2/2016 | Tabuteau |
| 2016/0030421 A1 | 2/2016 | Tabuteau |
| 2016/0128944 A1 | 5/2016 | Chawrai et al. |
| 2016/0128998 A1 | 5/2016 | Tabuteau |
| 2016/0136155 A1 | 5/2016 | Tabuteau |
| 2016/0199321 A1 | 7/2016 | Tabuteau |
| 2016/0228390 A1 | 8/2016 | Tabuteau |
| 2016/0263099 A1 | 9/2016 | Tabuteau |
| 2016/0263100 A1 | 9/2016 | Tabuteau |
| 2016/0317475 A1 | 11/2016 | Tabuteau |
| 2016/0317476 A1 | 11/2016 | Tabuteau |
| 2016/0324807 A1 | 11/2016 | Tabuteau |
| 2016/0339017 A1 | 11/2016 | Tabuteau |
| 2016/0346276 A1 | 12/2016 | Tabuteau |
| 2016/0361305 A1 | 12/2016 | Tabuteau |
| 2016/0375008 A1 | 12/2016 | Tabuteau |
| 2016/0375012 A1 | 12/2016 | Tabuteau |
| 2017/0007558 A1 | 1/2017 | Tabuteau |
| 2017/0014357 A1 | 1/2017 | Tabuteau |
| 2017/0252309 A1 | 9/2017 | Tabuteau |
| 2017/0281617 A1 | 10/2017 | Tabuteau |
| 2017/0304229 A1 | 10/2017 | Tabuteau |
| 2017/0304230 A1 | 10/2017 | Tabuteau |
| 2017/0304298 A1 | 10/2017 | Tabuteau |
| 2017/0354619 A1 | 12/2017 | Tabuteau |
| 2017/0360773 A1 | 12/2017 | Tabuteau |

(56) References Cited

U.S. PATENT DOCUMENTS

| | | |
|---|---|---|
| 2017/0360774 A1 | 12/2017 | Tabuteau |
| 2017/0360776 A1 | 12/2017 | Tabuteau |
| 2018/0092906 A1 | 4/2018 | Tabuteau |
| 2018/0116980 A1 | 5/2018 | Tabuteau |
| 2018/0133195 A1 | 5/2018 | Tabuteau |
| 2018/0207151 A1 | 7/2018 | Tabuteau |
| 2018/0256518 A1 | 9/2018 | Tabuteau |
| 2018/0360823 A1 | 12/2018 | Tabuteau |
| 2019/0000835 A1 | 1/2019 | Tabuteau |
| 2019/0008800 A1 | 1/2019 | Tabuteau |
| 2019/0008801 A1 | 1/2019 | Tabuteau |
| 2019/0008805 A1 | 1/2019 | Tabuteau |
| 2019/0015407 A1 | 1/2019 | Tabuteau |
| 2019/0083426 A1 | 3/2019 | Tabuteau |
| 2019/0142768 A1 | 5/2019 | Tabuteau |
| 2019/0192450 A1 | 6/2019 | Tabuteau |
| 2019/0192507 A1 | 6/2019 | Tabuteau |
| 2019/0216798 A1 | 7/2019 | Tabuteau |
| 2019/0216800 A1 | 7/2019 | Tabuteau |
| 2019/0216801 A1 | 7/2019 | Tabuteau |
| 2019/0290601 A1 | 9/2019 | Tabuteau |
| 2020/0022929 A1 | 1/2020 | Tabuteau |
| 2020/0093762 A1 | 3/2020 | Tabuteau |
| 2020/0147008 A1 | 5/2020 | Tabuteau |
| 2020/0147075 A1 | 5/2020 | Tabuteau |
| 2020/0206217 A1 | 7/2020 | Tabuteau |
| 2020/0215055 A1 | 7/2020 | Tabuteau |
| 2020/0215056 A1 | 7/2020 | Tabuteau |
| 2020/0215057 A1 | 7/2020 | Tabuteau |
| 2020/0215058 A1 | 7/2020 | Tabuteau |
| 2020/0215059 A1 | 7/2020 | Tabuteau |
| 2020/0222389 A1 | 7/2020 | Tabuteau |
| 2020/0230078 A1 | 7/2020 | Tabuteau |
| 2020/0230129 A1 | 7/2020 | Tabuteau |
| 2020/0230130 A1 | 7/2020 | Tabuteau |
| 2020/0230131 A1 | 7/2020 | Tabuteau |
| 2020/0237751 A1 | 7/2020 | Tabuteau |
| 2020/0237752 A1 | 7/2020 | Tabuteau |
| 2020/0246280 A1 | 8/2020 | Tabuteau |
| 2020/0261431 A1 | 8/2020 | Tabuteau |
| 2020/0297666 A1 | 9/2020 | Tabuteau |
| 2020/0338022 A1 | 10/2020 | Tabuteau |
| 2020/0360310 A1 | 11/2020 | Tabuteau |
| 2020/0397723 A1 | 12/2020 | Tabuteau |
| 2020/0397724 A1 | 12/2020 | Tabuteau |
| 2020/0405664 A1 | 12/2020 | Tabuteau |
| 2021/0000763 A1 | 1/2021 | Tabuteau |
| 2021/0000764 A1 | 1/2021 | Tabuteau |
| 2021/0000765 A1 | 1/2021 | Tabuteau |
| 2021/0000768 A1 | 1/2021 | Tabuteau |
| 2021/0000820 A1 | 1/2021 | Tabuteau |
| 2021/0015768 A1 | 1/2021 | Tabuteau |
| 2021/0015814 A1 | 1/2021 | Tabuteau |
| 2021/0015815 A1 | 1/2021 | Tabuteau |
| 2021/0023075 A1 | 1/2021 | Tabuteau |
| 2021/0023076 A1 | 1/2021 | Tabuteau |
| 2021/0030747 A1 | 2/2021 | Tabuteau |
| 2021/0030749 A1 | 2/2021 | Tabuteau |
| 2021/0030750 A1 | 2/2021 | Tabuteau |
| 2021/0030751 A1 | 2/2021 | Tabuteau |
| 2021/0046067 A1 | 2/2021 | Tabuteau |
| 2021/0052521 A1 | 2/2021 | Tabuteau |
| 2021/0060004 A1 | 3/2021 | Tabuteau |
| 2021/0060005 A1 | 3/2021 | Tabuteau |
| 2021/0069125 A1 | 3/2021 | Tabuteau |
| 2021/0069128 A1 | 3/2021 | Tabuteau |
| 2021/0077428 A1 | 3/2021 | Tabuteau |
| 2021/0077429 A1 | 3/2021 | Tabuteau |
| 2021/0077483 A1 | 3/2021 | Tabuteau |
| 2021/0106546 A1 | 4/2021 | Tabuteau |
| 2021/0177834 A1 | 6/2021 | Tabuteau |
| 2021/0186899 A1 | 6/2021 | Tabuteau |
| 2021/0186900 A1 | 6/2021 | Tabuteau |
| 2021/0186901 A1 | 6/2021 | Tabuteau |
| 2021/0186955 A1 | 6/2021 | Tabuteau |
| 2021/0186956 A1 | 6/2021 | Tabuteau |
| 2021/0196704 A1 | 7/2021 | Tabuteau |
| 2021/0196705 A1 | 7/2021 | Tabuteau |
| 2021/0205239 A1 | 7/2021 | Tabuteau |
| 2021/0205240 A1 | 7/2021 | Tabuteau |
| 2021/0205297 A1 | 7/2021 | Tabuteau |
| 2021/0220293 A1 | 7/2021 | Tabuteau |
| 2021/0220294 A1 | 7/2021 | Tabuteau |
| 2021/0220348 A1 | 7/2021 | Tabuteau |
| 2021/0260054 A1 | 8/2021 | Tabuteau |
| 2021/0267967 A1 | 9/2021 | Tabuteau |
| 2021/0338605 A1 | 11/2021 | Tabuteau |
| 2021/0346370 A1 | 11/2021 | Tabuteau |
| 2021/0361645 A1 | 11/2021 | Tabuteau |
| 2021/0401828 A1 | 12/2021 | Tabuteau |
| 2021/0401829 A1 | 12/2021 | Tabuteau |
| 2021/0401830 A1 | 12/2021 | Tabuteau |
| 2021/0401831 A1 | 12/2021 | Tabuteau |
| 2022/0008363 A1 | 1/2022 | Tabuteau |
| 2022/0071930 A1 | 3/2022 | Tabuteau |
| 2022/0071931 A1 | 3/2022 | Tabuteau |
| 2022/0079892 A1 | 3/2022 | Tabuteau |
| 2022/0096462 A1 | 3/2022 | Tabuteau |
| 2022/0105086 A1 | 4/2022 | Tabuteau |
| 2022/0133655 A1 | 5/2022 | Tabuteau |
| 2022/0142950 A1 | 5/2022 | Tabuteau |
| 2022/0193012 A1 | 6/2022 | Tabuteau |
| 2022/0218631 A1 | 7/2022 | Tabuteau |
| 2022/0218698 A1 | 7/2022 | Tabuteau |
| 2022/0233470 A1 | 7/2022 | Tabuteau |
| 2022/0233474 A1 | 7/2022 | Tabuteau |
| 2022/0233518 A1 | 7/2022 | Tabuteau |
| 2022/0233519 A1 | 7/2022 | Tabuteau |
| 2022/0241220 A1 | 8/2022 | Tabuteau |
| 2022/0241221 A1 | 8/2022 | Tabuteau |
| 2022/0241269 A1 | 8/2022 | Tabuteau |
| 2022/0241270 A1 | 8/2022 | Tabuteau |
| 2022/0265639 A1 | 8/2022 | Tabuteau |
| 2022/0280504 A1 | 9/2022 | Tabuteau |
| 2022/0313689 A1 | 10/2022 | Tabuteau |
| 2022/0323381 A1 | 10/2022 | Tabuteau |
| 2022/0378779 A1 | 12/2022 | Tabuteau |
| 2023/0045675 A1 | 2/2023 | Tabuteau |
| 2023/0096437 A1 | 3/2023 | Tabuteau |
| 2023/0099206 A1 | 3/2023 | Tabuteau |
| 2023/0100008 A1 | 3/2023 | Tabuteau |
| 2023/0100913 A1 | 3/2023 | Tabuteau |
| 2023/0114111 A1 | 4/2023 | Tabuteau |
| 2023/0131854 A1 | 4/2023 | Tabuteau |
| 2023/0142244 A1 | 5/2023 | Tabuteau |
| 2023/0210843 A1 | 7/2023 | Tabuteau |
| 2023/0218550 A1 | 7/2023 | Tabuteau |
| 2023/0225995 A1 | 7/2023 | Tabuteau |
| 2023/0233491 A1 | 7/2023 | Tabuteau |
| 2023/0241010 A1 | 8/2023 | Tabuteau |
| 2023/0248668 A1 | 8/2023 | Tabuteau |
| 2023/0248669 A1 | 8/2023 | Tabuteau |
| 2023/0255905 A1 | 8/2023 | Tabuteau |
| 2023/0263750 A1 | 8/2023 | Tabuteau |
| 2023/0270740 A1 | 8/2023 | Tabuteau |
| 2023/0277478 A1 | 9/2023 | Tabuteau |
| 2023/0277479 A1 | 9/2023 | Tabuteau |
| 2023/0277480 A1 | 9/2023 | Tabuteau |
| 2023/0277481 A1 | 9/2023 | Tabuteau |
| 2023/0293456 A1 | 9/2023 | Tabuteau |
| 2024/0000770 A1 | 1/2024 | Tabuteau |
| 2024/0016797 A1 | 1/2024 | Tabuteau |
| 2024/0024309 A1 | 1/2024 | Tabuteau |
| 2024/0041862 A1 | 2/2024 | Tabuteau |
| 2024/0041863 A1 | 2/2024 | Tabuteau |
| 2024/0050383 A1 | 2/2024 | Tabuteau |
| 2024/0066025 A1 | 2/2024 | Tabuteau |
| 2024/0115524 A1 | 4/2024 | Tabuteau |
| 2024/0148719 A1 | 5/2024 | Tabuteau |
| 2024/0156751 A1 | 5/2024 | Tabuteau |
| 2024/0165104 A1 | 5/2024 | Tabuteau |
| 2024/0189302 A1 | 6/2024 | Tabuteau |
| 2024/0197656 A1 | 6/2024 | Tabuteau |
| 2024/0197720 A1 | 6/2024 | Tabuteau |

(56) References Cited

U.S. PATENT DOCUMENTS

| | | |
|---|---|---|
| 2024/0238276 A1 | 7/2024 | Tabuteau |
| 2024/0252451 A1 | 8/2024 | Tabuteau |
| 2024/0269130 A1 | 8/2024 | Tabuteau |
| 2024/0299319 A1 | 9/2024 | Tabuteau |
| 2024/0299320 A1 | 9/2024 | Tabuteau |
| 2024/0307408 A1 | 9/2024 | Tabuteau |
| 2024/0390297 A1 | 11/2024 | Tabuteau |
| 2024/0408040 A1 | 12/2024 | Tabuteau |
| 2025/0009754 A1 | 1/2025 | Tabuteau |
| 2025/0012821 A1 | 1/2025 | Tabuteau |

FOREIGN PATENT DOCUMENTS

| | | |
|---|---|---|
| KR | 101612197 B1 | 4/2016 |
| WO | 1998050044 | 11/1998 |
| WO | 2003086362 A2 | 10/2003 |
| WO | 2004089873 A1 | 10/2004 |
| WO | 2009006194 | 1/2009 |
| WO | 2009050726 A2 | 4/2009 |
| WO | 2015069809 A1 | 5/2015 |
| WO | 2016125108 A1 | 8/2016 |
| WO | 2020146412 A1 | 7/2020 |
| WO | 2021202329 A1 | 10/2021 |
| WO | 2021202419 A1 | 10/2021 |
| WO | 2023004064 A1 | 1/2023 |

OTHER PUBLICATIONS

Auvelity (dextromethorphan hydrobromide and bupropion hydrochloride), Highlights of Prescribing Information and Medication Guide, issued Dec. 2022.

International Preliminary Report on Patentability, PCT/US2021/061492, mailed on Jun. 15, 2023.

International Search Report and Written Opinion, PCT/US2021/061492 received on Jun. 15, 2023.

International Search Report and Written Opinion, PCT/US2022/012768 received on Jul. 5, 2023.

International Search Report and Written Opinion, PCT/US2023/067062 mailed on Jul. 12, 2023.

Axsome Therapeutics Announces Topline Results of the Stride-1 Phase 3 Trial in Treatment Resistant Depression and Expert Call to Discuss Clinical Implications, Mar. 2020 (retrieved from internet on Jul. 19, 2023). <axsometherapeuticsinc.gcs-web.com/node/9176/pdf>.

Anderson, A.; et al. "Efficacy and Safety of AXS-05, an Oral NMDA Receptor Antagonist with Multimodal Activity, in Major Depressive Disorder: Results of a Phase 2, Double-Blind, Active-Controlled Trial" ASCP Annual Meeting 2019 (retrieved from internet on Jul. 19, 2023). <d3dyybxyjb4kyh.cloudfront.net/pdfs/SOBP+2021+AXS-05+MDD+Poster+FINAL.pdf> (May 2019).

O'Gorman, C; et al. "Rapid Effects of AXS 05, an Oral NMDA Receptor Antagonist, in Major Depressive Disorder: Results from Two Randomized, Double Blind, Controlled Trials" ASCP Annual Meeting 2021 (retrieved from internet on Jul. 19, 2023). <d3dyybxyjb4kyh.cloudfront.net/pdfs/SOBP+2021+AXS-05+MDD+Poster+FINAL.pdf> (Jun. 2021).

O'Gorman, C.; et al. "PMH40 Effects of AXS-05 on Patient Reported Depressive Symptoms in Major Depressive Disorder: Results from the Gemini Trial" <doi.org/10.1016/j.jval.2021.04.662> (retrieved from internet on Jul. 19, 2023). Value in Health, Jun. 2021, vol. 24, Supplement 1, pp. S135.

O'Gorman, C.; et al. "P246. Rapid Antidepressant Effects and MADRS Core Symptom Improvements With AXS-05, an Oral NMDA Receptor Antagonist, in Major Depressive Disorder: Results From Two Randomized, Double-Blind, Controlled Trials" ACNP 60th Annual Meeting: Poster Abstracts P246 <nature.com/articles/s41386-021-01236-7> (retrieved from internet on Jul. 19, 2023). Neuropsychopharmacol. 46 (Suppl 1), 72-217, Dec. 2021.

International Preliminary Report on Patentability, PCT/US2022/012768, mailed on Jul. 27, 2023.

Nofziger et al., Evaluation of dextromethorphan with select antidepressant therapy for the treatment of depression in the acute care psychiatric setting, Mental Health Clinician, 9(2), 76-81, Mar. 2019.

Update: Bupropion Hydrochloride Extended-Release 300 mg Bioequivalence Studies, FDA, retrieved Mar. 2021.

FDA Draft Guidance on Bupropion Hydrochloride, revised Mar. 2013.

Forfivo XL (bupropion hydrochloride) extended-release tablets, for oral use, Highlights of Prescribing Information, revised Dec. 2019.

Forfivo XL (Bupropion HCI) extended-release tablet, NDA 22497, Jan. 25, 2010.

Wellbutrin XL (bupropion hydrochloride extended-release), Highlights of Prescribing Information, revised Mar. 2022.

Baker T. E. et al., Human Milk and Plasma Pharmacokinetics of Single-Dose Rimegepant 75mg in Healthy Lactating Women, Breastfeeding Medicine, 17(3), 277-282, 2022.

Berle J. O. et al., Antidepressant Use During Breastfeeding, Current Women's Health Reviews, 7(1), 28-34, Feb. 2011.

Briggs G. G. et al., Excretion of bupropion in breast milk, Annals of Pharmacotherapy, 27(4):431-433, Apr. 1993.

Chad L. et al., Update on antidepressant use during breastfeeding, Canadian Family Physician, 59(6), 633-634, Jun. 2013.

Chaudron L. H. et al., Bupropion and Breastfeeding: A case of a possible Infant Seizure, The Journal of clinical psychiatry, 65(6), 881-882, Jun. 2004.

Davis M. F. et al., Bupropion Levels in Breast Milk for 4 Mother-Infant Pairs: More Answers to Lingering Questions, J. Clin. Psychiatry, 70(2), 297-298, Feb. 2009.

Di Scalea T. L. et al., Antidepressant Medication Use during Breastfeeding, Clinical obstetrics and gynecology, 52 (3): 483-497, Sep. 2009.

Dwoskin L. P. et al., Review of the Pharmacology and Clinical Profile of Bupropion, and Antidepressant and Tobacco Use Cessation Agent, CNS Drug Reviews, 12(3-4), 178-207, Sep. 2006.

Gentile S, The safety of newer antidepressants in pregnancy and breastfeeding, Drug Safety, 28(2), 137-152, Feb. 2005. [doi: 10.2165/00002018-200528020-00005. PMID: 15691224.].

Haas J. S. et al., Bupropion in breast milk: an exposure assessment for potential treatment to prevent post-partum tobacco use, Tobacco Control, 13(1), 52-56, Mar. 2004.

Ram D. et al., Antidepressants, anxiolytics, and hypnotics in pregnancy and lactation, Indian J Psychiatry, 57(Suppl 2): S354-S371, Jul. 2015. [doi:10.4103/0019-5545.161504].

Weissman A. M. et al., Pooled Analysis of Antidepressant Levels in Lactating Mothers, Breast Milk, and Nursing Infants, Am J Psychiatry, 161(6), 1066-1078, Jun. 2004.

Horn J. R. et al., Get to Know an Enzyme: CYP2D6, Pharmacy Times, Jul. 2008, retrieved on Aug. 28, 2023.

International Search Report and Written Opinion, PCT/US2023/069286 mailed on Aug. 22, 2023.

International Search Report and Written Opinion, PCT/US2023/069239 mailed on Aug. 28, 2023.

International Search Report and Written Opinion, PCT/US2023/069367 mailed on Aug. 28, 2023.

International Search Report and Written Opinion, PCT/US2023/069655 mailed on Sep. 15, 2023.

International Search Report and Written Opinion, PCT/US2023/069371 mailed on Sep. 26, 2023.

International Search Report and Written Opinion, PCT/US2022/037913 mailed on Sep. 21, 2022.

International Search Report and Written Opinion, PCT/US2022/074713 mailed on Sep. 21, 2022.

International Preliminary Report on Patentability, PCT/US2022/037913, issued on Jan. 18, 2024.

International Preliminary Report on Patentability, PCT/US2022/074713, issued on Feb. 22, 2024.

Chinese Pat. No. 202080004041.1 Invalidation Notice and Request issued on Jan. 15, 2024. (English translation included).

Ward K. and Citrome L.: "AXS-05: an investigational treatment for Alzheimer's disease-associated agitation", Expert Opinion on Investigational Drugs, Jul. 6, 2022, vol. 31, issue 8, pp. 773-780, DOI: 10.1080/13543784.2022.2096006.

(56) References Cited

OTHER PUBLICATIONS

Defendant Teva Pharmaceuticals, Inc.'s Invalidity Contentions for U.S. Pat. Nos. 11,752,144, 11,717,518, 11,730,706 and Exhibits A-C dated Apr. 11, 2024.
Goodnick, Psychotropic drugs and the ECG: focus on the QTc interval, Expert Opinion on Pharmacotherapy, vol. 3, No. 5, p. 479-498, 2002.
International Search Report and Written Opinion, PCT/US2024/046359 mailed on Nov. 28, 2024.
Tabuteau H, et al. "Effect of AXS-05 (Dextromethorphan-Bupropion) in Major Depressive Disorder: A Randomized Double-Blind Controlled Trial" Am J Psychiatry (2022) vol. 179 pp. 490-499. doi: 10.1176/appi.ajp.21080800.
International Preliminary Report on Patentability, PCT/US2023/067062, mailed on Nov. 28, 2024.
International Search Report and Written Opinion, PCT/US2024/043903 mailed on Nov. 28, 2024.
International Preliminary Report on Patentability, PCT/US2023/069286, mailed on Jan. 9, 2025.
International Preliminary Report on Patentability, PCT/US2023/069371, mailed on Jan. 9, 2025.
International Preliminary Report on Patentability, PCT/US2023/069655, mailed on Jan. 16, 2025.

\* cited by examiner

BUPROPION AND DEXTROMETHORPHAN FOR REDUCTION OF SUICIDE RISK IN DEPRESSION PATIENTS

CROSS-REFERENCE TO RELATED APPLICATIONS

This application is a continuation of U.S. patent application Ser. No. 18/323,714, filed May 25, 2023; which is a continuation of International Pat. App. No. PCT/US2021/061492, filed Dec. 1, 2021; which claims the benefit of U.S. Provisional App. Nos. 63/120,160, filed Dec. 1, 2020, 63/120,672, filed Dec. 2, 2020, and 63/122,902, filed Dec. 8, 2020; all of which are incorporated by reference herein in their entireties.

SUMMARY

This disclosure relates to a method of treating depression and/or reducing risk of suicide, comprising administering combination of about 90 mg to about 120 mg of bupropion hydrochloride, or a molar equivalent amount of another form of bupropion, and about 40 mg to about 50 mg of dextromethorphan hydrobromide, or a molar equivalent amount of another form of dextromethorphan. The combination may be administered twice a day to a human being suffering from major depressive disorder and having a score of 3 or greater on the Suicidality Item of the Montgomery-Åsberg Depression Rating Scale (MADRS-SI).

DETAILED DESCRIPTION

The combination of dextromethorphan and bupropion may be used to treat depression, such as major depressive disorder and/or reduce the risk of suicide. Patients being treated by this combination may suffer from depression and may have a score of 2 or greater, or 3 or greater on the Suicidality Item of the Montgomery-Åsberg Depression Rating Scale (MADRS-SI).

Dextromethorphan is rapidly metabolized in the human liver. This rapid hepatic metabolism may limit systemic drug exposure in individuals who are extensive metabolizers. Human beings can be: 1) extensive metabolizers of dextromethorphan—those who rapidly metabolize dextromethorphan; 2) poor metabolizers of dextromethorphan—those who only poorly metabolize dextromethorphan; or 3) intermediate metabolizers of dextromethorphan—those whose metabolism of dextromethorphan is somewhere between that of an extensive metabolizer and a poor metabolizer. Extensive metabolizers can also be ultra-rapid metabolizers. Non-poor metabolizers of dextromethorphan include extensive metabolizers of dextromethorphan and intermediate metabolizers of dextromethorphan. Extensive metabolizers of dextromethorphan are a significant portion of the human population. Dextromethorphan can, for example, be metabolized to dextrorphan.

When given the same oral dose of dextromethorphan, plasma levels of dextromethorphan are significantly higher in poor metabolizers or intermediate metabolizers as compared to extensive metabolizers of dextromethorphan. The low plasma concentrations of dextromethorphan can limit its clinical utility as a single agent for extensive metabolizers, and possibly intermediate metabolizers, of dextromethorphan. Bupropion inhibits the metabolism of dextromethorphan, and raises the plasma concentration of dextromethorphan, and can thus improve its therapeutic efficacy. Similarly, bupropion may allow dextromethorphan to be given less often or in a lower amount, such as once a day instead of twice a day, once a day instead of three times a day, once a day instead of four times a day, twice a day instead of three times a day, or twice a day instead of four times a day, without loss of therapeutic efficacy.

The MADRS is a clinician-rated scale. The MADRS is used to assess depressive symptomatology during the previous week. Subjects are rated on 10 items to assess symptoms: 1) apparent sadness, 2) reported sadness, 3) inner tension, 4) reduced sleep, 5) reduced appetite, 6) concentration difficulties, 7) lassitude, 8) inability to feel, 9) pessimistic thoughts, 10) suicidal thoughts. Each item yields a score of 0 to 6.

The overall score ranges from 0 to 60. A score of 0 indicates the absence of symptoms, and a score of 60 indicates symptoms of maximum severity. A total score ranging from 0 to 6 indicates that the patient is in the normal range (no depression), a score ranging from 7 to 19 indicates "mild depression," 20 to 34 indicates "moderate depression," a score of 35 and greater indicates "severe depression."

In some embodiments, the human being that is treated with a combination of dextromethorphan and bupropion, e.g. for a type of depression, has, or is selected for having, a MADRS score that is at least about 20, at least about 25, at least about 30, at least about 35, at least about 40, at least about 45, at least about 50, at least about 55, about 20-25, about 25-30, about 30-35, about 35-40, about 40-45, about 45-50, about 50-55, about 55-60, about 25-35, about 35-45, about 45-60, about 25-40, or about 40-60.

In some embodiments, treatment with the combination of dextromethorphan and bupropion results in the human being having a MADRS score that is reduced by at least about 10%, at least about 20%, at least about 30%, at least about 40%, at least about 50%, about 10-20%, about 20-30%, about 30-40%, about 40-50%, about 50-60%, about 60-80%, about 80-90%, or about 90-100% as compared to baseline or placebo. In some embodiments, the reduction is compared to baseline. In some embodiments, the reduction is compared to placebo. In some embodiments, the reduction is compared to the baseline before treatment.

In some embodiments, treatment with the combination of dextromethorphan and bupropion results in the human being having a MADRS score that is less than 34, about 20-34, about 7-19, about 0-6, about 30 or less, about 26 or less, about 25 or less, about 20 or less, about 19 or less, about 17 or less, about 14 or less, about 12 or less, about 10 or less, about 8 or less, about 6 or less, about 5 or less, about 4 or less, about 3 or less, about 2 or less, about 1 or less, about 0, about 7 or less, about 0-6, about 1-2, about 2-3, about 3-4, about 4-5, about 5-6, about 6-7, about 7-8, about 8-9, about 9-10, about 10-11, about 11-12, about 12-13, about 13-14, about 14-15, about 15-16, about 16-17, about 17-18, about 18-19, about 19-20, about 18-20, about 1-3, about 3-6, about 6-9, about 9-12, about 12-14, about 12-15, about 15-19, or about 15-20.

Depression may be manifested by depressive symptoms. These symptoms may include psychological changes such as changes in mood, feelings of intense sadness, despair, mental slowing, loss of concentration, pessimistic worry, agitation, anxiety, irritability, guilt, anger, feelings of worthlessness, reckless behavior, suicidal thoughts or attempts, and/or self-deprecation. Physical symptoms of depression may include insomnia, anorexia, appetite loss, weight loss, weight gain, decreased energy and libido, fatigue, restlessness, aches, pains, headaches, cramps, digestive issues, and/or abnormal hormonal circadian rhythms.

Some patients, even after treatment with medications such as antidepressants, may have an inadequate or no response to the treatment. Treatment resistant depression (TRD), or treatment-refractory depression, is a condition generally associated with patients who have failed treatment with at least two antidepressants. Part of the diagnosis for TRD is for the patient to have had an inadequate response to treatment with the antidepressants after an adequate dose and adequate course, e.g. in the current depressive episode. TRD may be more difficult to treat due to the comorbidity of other medical or psychological illnesses, such as drug/alcohol abuse or eating disorders, or TRD being misdiagnosed. Some TRD patients have had an inadequate response to 1, 2, 3, or more adequate antidepressant treatment trials or have failed or had an inadequate response to 1, 2, 3, or more prior antidepressant treatments. In some embodiments, a patient being treated for treatment resistant depression has failed treatment with at least 1, 2, 3, 4, 5, 6, 7, 8, 9, 10, or more antidepressant therapies. In addition to other depressed patients, the combination of bupropion and dextromethorphan may be effective in treating patients suffering from treatment resistant depression with suicidal ideation.

Patients who may benefit from the treatments described herein include pediatric patients, such as patients under about 18 years of age, about 0-5 years of age, about 5-10 years of age, about 10-12 years of age, or about 12-18 years of age; adult patients, such as patients having an age of about 18-70 years, about 18-65 years, about 18-30 years, about 18-20 years, about 20-30 years, about 30-40 years, about 40-50 years, about 50-60 years, about 60-70 years, about 70-80 years, about 80-90 years, about 30-50 years, about 50-65 years; elderly patients, such as patients over 65 years of age, about 65-75 years of age, about 75-90 years of age, or over 90 years of age; and about 41 years of age or older.

In some embodiments, the human being that is treated with a combination of dextromethorphan and bupropion, e.g. for a type of depression, is, or is selected for being, of Asian descent. In some embodiments, the human being that is treated with a combination of dextromethorphan and bupropion, e.g. for a type of depression, is, or is selected for being, of Japanese descent. In some embodiments, the human being that is treated with a combination of dextromethorphan and bupropion, e.g. for a type of depression, is, or is selected for being, of Korean descent. In some embodiments, the human being that is treated with a combination of dextromethorphan and bupropion, e.g. for a type of depression, is, or is selected for being, of Chinese descent. The assignment of an individual as having Asian, Chinese, Japanese, or Korean descent may be based upon self-reporting by the individual. In these Asian individuals, the combination of dextromethorphan and bupropion may be effective for treating depression where bupropion alone is not effective for treating depression. This may be of particular importance because patients of Asian descent may suffer from more severe depression than those of other ethnic or cultural groups.

In some embodiments, the human being that is treated with a combination of dextromethorphan and bupropion, e.g. for a type of depression, is suffering from, or is selected for suffering from, a major depressive episode that has lasted between about 8 weeks and about 24 months, about 1-6 months, about 6-12 months, about 1-2 years, at least about 1 week, at least about 2 weeks, at least about 3 weeks, at least about 4 weeks, at least about 6 weeks, at least 7 weeks, at least about 2 months, at least about 3 months, at least about 4 months, at least about 5 months, at least about 6 months, at least about 9 months, at least about 1 year, at least about 18 months, at least about 2 years, about 1-12 weeks, about 3-6 months, about 6-9 months, about 9-12 months, about 12-18 months, about 18-24 months, about 2-4 years, about 4-6 years, about 6-10 years, about 10-20 years or longer.

In some embodiments, the human being that is treated with a combination of dextromethorphan and bupropion, e.g. for a type of depression, has, or is selected having, about 1-100, or more, lifetime depressive episodes, such as a major depressive episodes, including at least 1, at least 2, at least 3, at least 4, at least 5, at least 6, at least 7, at least 10, at least 15, at least 20, at least 30, at least 40, at least 50, at least 60, at least 70, at least 80, at least 90, at least 100, 1-5, 5-10, 10-20, 20-30, 30-40, 40-50, 50-60, 60-70, 70-80, 80-90, 90-100, or 4-7 lifetime depressive episodes.

In some embodiments, the human being that is treated with a combination of dextromethorphan and bupropion, e.g. for a type of depression, has, or is selected for having, an inadequate response to one or more prior antidepressant therapies, e.g. 1, 2, 3, 4, 5 or more prior antidepressant therapies, including prior antidepressant therapies in the current depressive episode (e.g. the current major depressive episode).

In some embodiments, the human being that is treated with a combination of dextromethorphan and bupropion, e.g. for a type of depression, is, or is selected for being male. In some embodiments, the human being that is treated with a combination of dextromethorphan and bupropion, e.g. for a type of depression, is, or is selected for being female.

The combination of bupropion and dextromethorphan is administered once a day or twice a day for at least one week, at least two weeks, at least three weeks, at least four weeks, at least six weeks, at least eight weeks, at least three months, at least four months, at least five months, or at least six months; and/or may be administered for up to four months, up to six months, up to one year, up to two years, or longer. In some embodiments, the combination of bupropion and dextromethorphan is administered twice a day for at least one week, at least two weeks, at least three weeks, at least four weeks, at least six weeks, at least eight weeks, at least three months, at least four months, at least five months, or at least six months; and/or may be administered for up to four months, up to six months, up to one year, up to two years, or longer. In some embodiments, the combination of bupropion and dextromethorphan is administered once a day for 1, 2, 3, 4, 5, 6, or 7 days, and then administered twice a day thereafter.

In some embodiments, at least about 50 mg, at least about 70 mg, at least about 90 mg, at least about 100 mg, at least about 110 mg, or at least about 120 mg of bupropion hydrochloride, or a molar equivalent amount of another form of bupropion (such as another salt form or the free base form) is administered once a day or twice a day. In some embodiments, the bupropion is administered once a day for 1, 2, 3, 4, 5, 6, or 7 days, and then administered twice a day thereafter.

In some embodiments, up to about 70 mg, up to about 90 mg, up to about 100 mg, up to about 110 mg, up to about 120 mg up to about 130 mg, or up to about 150 mg, of bupropion hydrochloride, or a molar equivalent amount of another form of bupropion (such as another salt form or the free base form) is administered once a day or twice a day. In some embodiments, the bupropion is administered once a day for 1, 2, 3, 4, 5, 6, or 7 days, and then administered twice a day thereafter.

In some embodiments, about 0.8x mg to about 1.2x mg of bupropion hydrochloride, or a molar equivalent amount of another form of bupropion (such as another salt form or the free base form) is administered once or twice a day, wherein x is about 50 mg (e.g. 40-60 mg), about 60 mg, about 70 mg, about 80 mg, about 90 mg, about 100 mg, about 120 mg, or about 140 mg. In some embodiments, the bupropion is administered once a day for 1, 2, 3, 4, 5, 6, or 7 days, and then administered twice a day thereafter.

In some embodiments, about 50-150 mg, about 90-120 mg, about 100-110 mg, or about 105 mg of bupropion hydrochloride, or a molar equivalent amount of another form of bupropion (such as another salt form or the free base form) is administered once a day or twice a day. In some embodiments, the bupropion is administered once a day for 1, 2, 3, 4, 5, 6, or 7 days, and then administered twice a day thereafter.

In some embodiments, at least about 30 mg, at least about 35 mg, at least about 40 mg, or about 45 mg of dextromethorphan hydrobromide, or a molar equivalent amount of another form of dextromethorphan (such as another salt form or the free base form) is administered once a day or twice a day. In some embodiments, the dextromethorphan is administered once a day for 1, 2, 3, 4, 5, 6, or 7 days, and then administered twice a day thereafter.

In some embodiments, up to about 50 mg, up to about 55 mg, up to about 60 mg, or up to about 45 mg of dextromethorphan hydrobromide, or a molar equivalent amount of another form of dextromethorphan (such as another salt form or the free base form) is administered once a day or twice a day. In some embodiments, the dextromethorphan is administered once a day for 1, 2, 3, 4, 5, 6, or 7 days, and then administered twice a day thereafter.

In some embodiments, about 0.8x mg to about 1.2x mg of dextromethorphan hydrobromide, or a molar equivalent amount of another form of dextromethorphan (such as another salt form or the free base form) is administered once a day or twice a day, wherein x is about 30 mg (e.g. 24-36 mg), about 40 mg, about 50 mg, or about 60 mg. In some embodiments, the dextromethorphan is administered once a day for 1, 2, 3, 4, 5, 6, or 7 days, and then administered twice a day thereafter.

In some embodiments, about 30-60 mg, about 40-50 mg, about 44-46 mg, or about 45 mg of dextromethorphan hydrobromide, or a molar equivalent amount of another form of dextromethorphan (such as another salt form or the free base form) is administered once a day or twice a day. In some embodiments, the dextromethorphan is administered once a day for 1, 2, 3, 4, 5, 6, or 7 days, and then administered twice a day thereafter.

Administration of the combination of bupropion and dextromethorphan may improve depression symptoms, such as the Montgomery-Åsberg Depression Rating Scale (MADRS) score. It may also reduce the Suicidality Item of the MADRS (MADRS-SI), such as by at least about 10%, at least about 20%, at least about 30%, at least about 40%, at least about 50%, at least about 60%, at least about 80%, or up to about 100%, e.g. after the combination is administered daily, such as twice a day, for one week, two weeks, four weeks, six weeks, eight weeks, or twelve weeks, etc.

In some embodiments, after eight days of receiving the combination of bupropion and dextromethorphan twice a day, the $C_{max}$ of dextromethorphan in the human being is increased about 15- to about 25-fold as compared to administration of 60 mg of dextromethorphan hydrobromide without bupropion or as compared to administration of a single dose of the combination of bupropion and dextromethorphan.

In some embodiments, after eight days of receiving the combination of bupropion and dextromethorphan twice a day, the $C_{min}$ of dextromethorphan in the human being is increased about 35- to about 45-fold as compared to administration of 60 mg of dextromethorphan hydrobromide without bupropion or as compared to administration of a single dose of the combination of bupropion and dextromethorphan.

In some embodiments, after eight days of receiving the combination of bupropion and dextromethorphan twice a day, the $AUC_{0-12}$ of dextromethorphan in the human being is increased about 25- to about 45-fold as compared to administration of 60 mg of dextromethorphan hydrobromide without bupropion or as compared to administration of a single dose of the combination of bupropion and dextromethorphan.

In some embodiments, after eight days of receiving the combination of bupropion and dextromethorphan twice a day, the $C_{max}$ of dextromethorphan in the human being is about 75-80 ng/ml.

In some embodiments, after eight days of receiving the combination of bupropion and dextromethorphan twice a day, the $C_{min}$ of dextromethorphan is about 42-50 ng/mL.

In some embodiments, after eight days of receiving the combination of bupropion and dextromethorphan twice a day, the $AUC_{0-12}$ of dextromethorphan in the human being is about 755 ng·hr/mL.

In some embodiments, after eight days of receiving the combination of bupropion and dextromethorphan twice a day, the $C_{max}$ of bupropion in the human being is about 85-90 ng/ml.

In some embodiments, after eight days of receiving the combination of bupropion and dextromethorphan twice a day, the $C_{min}$ of bupropion is about 25-35 ng/ml.

In some embodiments, after eight days of receiving the combination of bupropion and dextromethorphan twice a day, the $AUC_{0-12}$ of bupropion in the human being is about 660-670 ng·hr/mL.

Example 1

An open label Phase III clinical trial was conducted using a tablet containing 45 mg dextromethorphan hydrobromide and 105 mg of bupropion hydrochloride with modulated delivery. This tablet was administered twice a day to patients suffering from major depressive disorder. A total of 611 patients participated in the trial, and a total of 597 patients were treated for at least 6 months when the trial was concluded. The mean MADRS score of the total patient population was 32.7 prior to treatment. The results for the total patient population are summarized in Table 1.

TABLE 1

| MADRS reduction for all patients after treatment | |
|---|---|
| Timepoint | MADRS Reduction-all patients |
| Baseline | 0 |
| 1 week | −10.4 |
| 2 weeks | −14.7 |
| 6 weeks | −20.6 |

A total of 37 of these patients suffered from major depressive disorder with suicidal ideation, defined as a score of ≥3 on the Suicidality Item of the Montgomery-Åsberg Depression Rating Scale (MADRS-SI). For the patients with suicidal ideation, the mean MADRS score was 36.8 and the mean MADRS-SI score was 3.4 prior to treatment. The results for these patients are summarized in Table 2.

TABLE 2

MADRS reduction for suicidal ideation patients after treatment

| Timepoint | MADRS Reduction-suicidal ideation patients |
|---|---|
| Baseline | 0 |
| 1 week | −12.9 |
| 2 weeks | −17.8 |
| 6 weeks | −22.8 |

Additionally, in the patients who suffered from suicidal ideation, the MADRS-SI score was reduced by 67.1% at the end of 1 week of treatment, 73.5% at the end of 2 weeks of treatment, and 82.4% at the end of 4 weeks of treatment as compared with baseline. This is potentially lifesaving because it shows a quick reduction in the risk of suicide.

The invention claimed is:

1. A method of treating depression and reducing risk of suicide, comprising selecting a human being suffering from major depressive disorder and having a score of 3 or greater on the Suicidality Item of the Montgomery-Åsberg Depression Rating Scale (MADRS-SI) and a score of at least 35 on the Montgomery-Åsberg Depression Rating Scale (MADRS), and administering a combination of about 90 mg to about 120 mg of bupropion hydrochloride, or a molar equivalent amount of another form of bupropion, and about 40 mg to about 50 mg of dextromethorphan hydrobromide, or a molar equivalent amount of another form of dextromethorphan, to a human being; wherein the combination is administered twice a day to the human being.

2. The method of claim 1, wherein the combination comprises about 105 mg of bupropion hydrochloride, or a molar equivalent amount of another form of bupropion, and about 45 mg of dextromethorphan hydrobromide, or a molar equivalent amount of another form of dextromethorphan.

3. The method of claim 1, wherein the combination is administered twice a day for at least one week.

4. The method of claim 1, wherein the combination is administered twice a day for at least two weeks.

5. The method of claim 1, wherein the combination is administered twice a day for at least six weeks.

6. The method of claim 1, wherein the MADRS-SI of the human being is reduced by at least 30% after the combination is administered to the human being twice a day for one week.

7. The method of claim 1, wherein the MADRS-SI of the human being is reduced by at least 50% after the combination is administered to the human being twice a day for two weeks.

8. The method of claim 1, wherein the MADRS-SI of the human being is reduced by at least 60% after the combination is administered to the human being twice a day for four weeks.

9. The method of claim 1, wherein after eight days of administration of the combination twice a day, the $C_{max}$ of dextromethorphan in the human being is increased about 15- to about 25-fold as compared to administration of a single dose of the combination.

10. The method of claim 1, wherein after eight days of administering the combination twice a day, the $C_{min}$ of dextromethorphan in the human being is increased about 35- to about 45-fold as compared to administering a single dose of the combination.

11. The method of claim 1, wherein after eight days of administering the combination twice a day, the $AUC_{0-12}$ of dextromethorphan in the human being is increased about 25- to about 45-fold as compared to administering a single dose of the combination.

12. The method of claim 2, wherein after eight days of administering the combination twice a day, the $C_{max}$ of dextromethorphan in the human being is about 75 ng/ml to about 80 ng/ml.

13. The method of claim 2, wherein after eight days of administering the combination twice a day, the $C_{min}$ of dextromethorphan is about 42 ng/ml to about 50 ng/mL.

14. The method of claim 2, wherein after eight days of administering the combination twice a day, the $AUC_{0-12}$ of dextromethorphan in the human being is about 755 ng·hr/mL.

15. The method of claim 2, wherein after eight days of administering the combination twice a day, the $C_{max}$ of bupropion in the human being is about 85 ng/ml to about 90 ng/ml.

16. The method of claim 2, wherein after eight days of administering the combination twice a day, the $C_{min}$ of bupropion is about 25 ng/ml to about 35 ng/ml.

17. The method of claim 2, wherein after eight days of administering the combination twice a day, the $AUC_{0-12}$ of bupropion in the human being is about 660 ng·hr/mL to about 670 ng·hr/mL.

\* \* \* \* \*